(12) United States Patent
Hagihara (10) Patent No.: US 10,856,723 B2
(45) Date of Patent: Dec. 8, 2020

(54) MEDICAL CIRCUIT BOARD AND MEDICAL DEVICE

(71) Applicant: Sony Olympus Medical Solutions Inc., Tokyo (JP)

(72) Inventor: Masahiro Hagihara, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/154,786

(22) Filed: Oct. 9, 2018

(65) Prior Publication Data
US 2019/0150708 A1 May 23, 2019

(30) Foreign Application Priority Data
Nov. 17, 2017 (JP) .................. 2017-222250

(51) Int. Cl.
| | |
|---|---|
| *H05K 1/00* | (2006.01) |
| *H05K 1/18* | (2006.01) |
| *H05K 7/00* | (2006.01) |
| *A61B 1/00* | (2006.01) |
| *H05K 5/06* | (2006.01) |
| *H05K 1/11* | (2006.01) |
| *G01M 3/16* | (2006.01) |
| *A61B 90/70* | (2016.01) |

(52) U.S. Cl.
CPC ...... *A61B 1/00055* (2013.01); *A61B 1/00124* (2013.01); *G01M 3/16* (2013.01); *H05K 1/11* (2013.01); *H05K 1/181* (2013.01); *H05K 5/065* (2013.01); *A61B 2090/701* (2016.02); *H05K 2201/09381* (2013.01); *H05K 2201/09418* (2013.01); *H05K 2201/10151* (2013.01)

(58) Field of Classification Search
CPC ............ A61B 1/00055; A61B 1/00124; A61B 2090/701; G01M 3/16; H05K 1/11; H05K 1/181; H05K 2201/09381; H05K 2201/09418; H05K 2201/10151; H05K 5/065
See application file for complete search history.

(56) References Cited

U.S. PATENT DOCUMENTS

| | | | |
|---|---|---|---|
| 6,998,861 B2 * | 2/2006 | Nakai .................. | H05K 1/111 361/761 |
| 2005/0127830 A1 * | 6/2005 | Heo .................... | H01L 27/3288 313/505 |

(Continued)

FOREIGN PATENT DOCUMENTS

JP    2012-139408    7/2012

*Primary Examiner* — Yuriy Semenenko
(74) *Attorney, Agent, or Firm* — Xsensus LLP (57) ABSTRACT

A medical circuit board includes a substrate on which a wiring pattern is formed, a plurality of electronic components mounted in a mounting area on the substrate, a resinous sealing member covering the plurality of electronic components, with which the plurality of electronic components are sealed to the substrate, and a detection unit provided in an area other than the mounting area on the substrate and detecting an infiltration of a liquid from an interface between the substrate and the sealing member into the mounting area. At least a part of the detection unit is covered with the sealing member and sealed with the sealing member to the substrate.

13 Claims, 10 Drawing Sheets

(56) References Cited

U.S. PATENT DOCUMENTS

| | | | | |
|---|---|---|---|---|
| 2009/0219041 A1* | 9/2009 | Wada | ............... | A61F 13/42 |
| | | | | 324/694 |
| 2014/0077824 A1* | 3/2014 | Niimi | ............... | G01N 27/121 |
| | | | | 324/664 |
| 2014/0168909 A1* | 6/2014 | Zheng | ............... | H05K 1/111 |
| | | | | 361/743 |
| 2014/0293211 A1* | 10/2014 | Terao | ............... | G02F 1/1339 |
| | | | | 349/153 |
| 2015/0002761 A1* | 1/2015 | Tsurusaki | ............... | G06F 1/1643 |
| | | | | 349/12 |
| 2015/0313015 A1* | 10/2015 | Wada | ............... | H01L 23/49811 |
| | | | | 174/261 |
| 2015/0362449 A1* | 12/2015 | Suzuki | ............... | G01N 27/121 |
| | | | | 257/40 |
| 2017/0082572 A1* | 3/2017 | Jiao | ............... | B64C 1/1484 |
| 2019/0189951 A1* | 6/2019 | Ren | ............... | G01N 27/121 |
| 2019/0237963 A1* | 8/2019 | Wuerstlein | ............... | H02H 7/0833 |

\* cited by examiner

MEDICAL CIRCUIT BOARD AND MEDICAL DEVICE

CROSS-REFERENCE TO RELATED APPLICATION

The present application claims priority to and incorporates by reference the entire contents of Japanese Patent Application No. 2017-222250 filed in Japan on Nov. 17, 2017.

BACKGROUND

The present disclosure relates to a medical circuit board and a medical device.

In the medical field, a medical endoscope apparatus (electronic endoscope) that captures an inside of a subject (inside of a living body) such as a human being and observes the inside of the living body has been known (see, for example, Japanese Laid-open Patent Publication No. 2012-139408).

In the medical endoscope apparatus described in Japanese Laid-open Patent Publication No. 2012-139408, a medical circuit board (circuit board) on which a plurality of electronic components (including a driving circuit of an image sensor for capturing the inside of the living body) are mounted in a connector connected to an external device such as a processor has been provided.

SUMMARY

Meanwhile, when a liquid such as moisture infiltrates into a connector, the liquid is likely to bring about problems in reliability of a plurality of electronic components (medical circuit board).

In particular, the connector described in Japanese Laid-open Patent Publication No. 2012-139408 is used in the medical endoscope apparatus for observing the inside of the living body. Since such a medical endoscope apparatus is subjected to sterilization treatment by a so-called autoclave or disinfection treatment by a disinfectant solution or the like before observing the inside of the living body, liquids such as steam (moisture) and the disinfectant solution easily infiltrate into the connector.

A medical circuit board according to one aspect of the preset disclosure includes: a substrate on which a wiring pattern is formed; a plurality of electronic components mounted in a mounting area on the substrate; a resinous sealing member covering the plurality of electronic components, with which the plurality of electronic components are sealed to the substrate; and a detection unit provided in an area other than the mounting area on the substrate and detecting an infiltration of a liquid into an interface between the substrate and the sealing member, wherein at least a part of the detection unit is covered with the sealing member and sealed with the sealing member between the sealing member and the substrate.

DETAILED DESCRIPTION

Hereinafter, a mode (hereinafter referred to as "embodiment") for carrying out the present disclosure will be described with reference to the accompanying drawings. It is to be noted that the present disclosure is not limited to embodiments to be described below. Further, in the description of the drawings, the same reference numerals are attached to the same parts.

First Embodiment

Schematic Configuration of Medical Endoscope Apparatus

Figure 1:
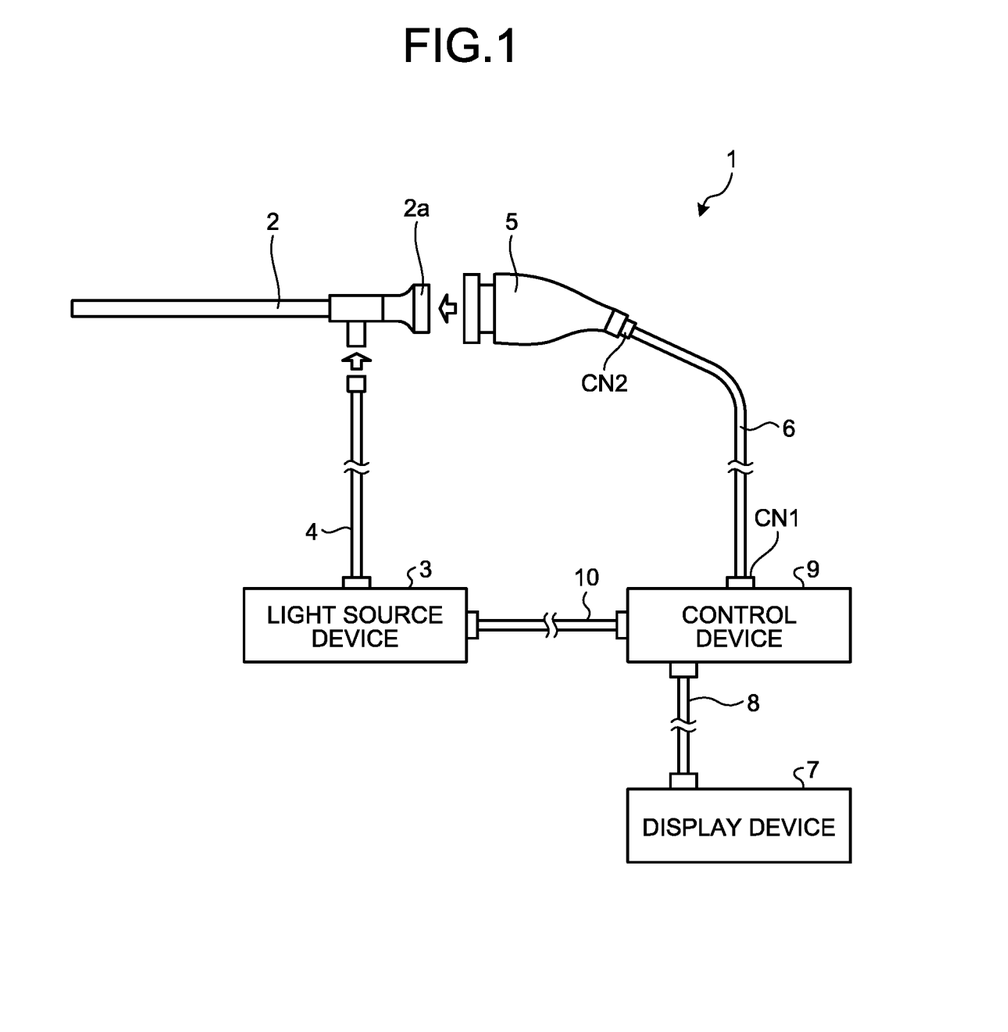
FIG. 1 is a diagram illustrating a schematic configuration of a medical endoscope apparatus according to a first embodiment.

FIG. 1 is a diagram illustrating a schematic configuration of a medical endoscope apparatus 1 according to a first embodiment.

The medical endoscope apparatus 1 corresponds to a medical device according to the present disclosure. The medical endoscope apparatus 1 is used in the medical field and is an apparatus for observing a subject such as an inside of a living body. As illustrated in FIG. 1, the medical endoscope apparatus 1 includes an insertion unit 2, a light source device 3, a light guide 4, a camera head 5, a first transmission cable 6, a display device 7, a second transmission cable 8, a control device 9, and a third transmission cable 10.

In the first embodiment, the insertion unit 2 is constituted by a rigid endoscope. That is, the insertion unit 2 is a hard elongated shape or at least partially soft elongated shape and is inserted into a living body. The insertion unit 2 is configured to include one or a plurality of lenses, and an optical system that condenses a subject image.

The light source device 3 is connected to one end of the light guide 4, and supplies illumination light, which illuminates the inside of the living body, to one end of the light guide 4 under the control of the control device 9.

One end of the light guide 4 is detachably connected to the light source device 3 and the other end of the light guide 4 is detachably connected to the insertion unit 2. The light guide 4 transmits light supplied from the light source device 3 from one end to the other end and supplies the light to the insertion unit 2. The light supplied to the insertion unit 2 is emitted from a distal end of the insertion unit 2 and irradiated into a living body. The light (subject image) irradiated into the living body and reflected from the living body is condensed by the optical system in the insertion unit 2.

The camera head 5 is detachably connected to a proximal end of the insertion unit 2 (eyepiece unit 2a (FIG. 1)). The camera head 5 captures the subject image condensed by the insertion unit 2 under the control of the control device 9, and outputs an image signal (RAW signal) by the capturing. In the first embodiment, the image signal is an image signal of 4K or more.

Both ends of the first transmission cable 6 are provided with connectors CN1 and CN2, and the connector CN1 (FIG. 1) at one end of the first transmission cable 6 is detachably connected to the control device 9 and the connector CN2 (FIG. 1) at the other end of the first transmission cable 6 is detachably connected to the camera head 5. The first transmission cable 6 transmits the image signal output from the camera head 5 to the control device 9 and transmits a control signal, a synchronization signal, a clock, driving power and the like, which are output from the control device 9, respectively, to the camera head 5.

The image signal from the camera head 5 to the control device 9 via the first transmission cable 6 may be transmitted as an optical signal or an electrical signal. The transmission of the control signal, the synchronization signal, and the clock from the control device 9 to the camera head 5 via the first transmission cable 6 is also the same.

In the first embodiment, a medical circuit board 11 is disposed inside the connector CN1 or/and the connector CN2 (see FIGS. 2 to 5). A detailed configuration of the medical circuit board 11 will be described below.

The display device 7 is constituted by a display using liquid crystal, organic electroluminescence (EL) or the like, and displays an image based on a video signal processed by the control device 9.

One end of the second transmission cable 8 is detachably connected to the control device 9 and the other end of the second transmission cable 8 is detachably connected to the display device 7. The second transmission cable 8 transmits the video signal from the control device 9 to the display device 7.

The control device 9 is configured to include a central processing unit (CPU) and the like, and collectively controls the operation of the light source device 3, the camera head 5, and the display device 7.

Specifically, the control device 9 generates the video signal by performing predetermined processing on the image signal acquired from the camera head 5 via the first transmission cable 6, and outputs the video signal via the second transmission cable 8 to the display device 7. The display device 7 displays an image based on the video signal. In addition, the control device 9 outputs the control signal or the like to the camera head 5 or the light source device 3 via the first and third transmission cables 6 and 10.

One end of the third transmission cable 10 is detachably connected to the light source device 3 and the other end of the third transmission cable 10 is detachably connected to the control device 9. The third transmission cable 10 transmits the control signal from the control device 9 to the light source device 3.

Configuration of Medical Circuit Board

Next, the configuration of the medical circuit board 11 will be described with reference to FIGS. 2 to 5.

Figure 2:
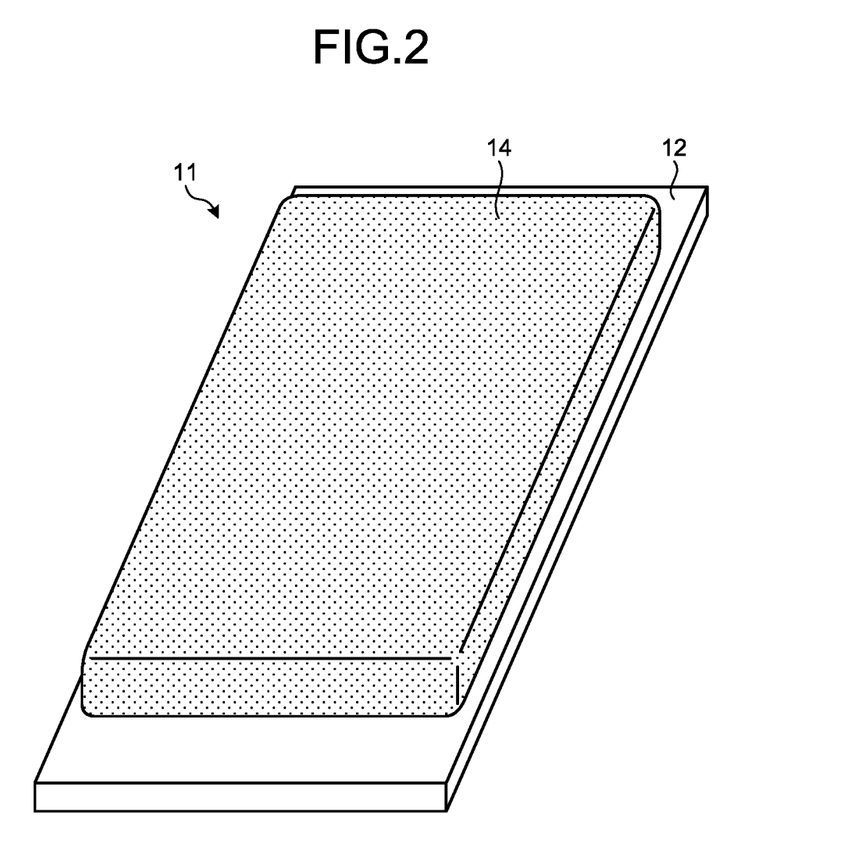
FIG. 2 is a diagram illustrating a medical circuit board.
Figure 3:
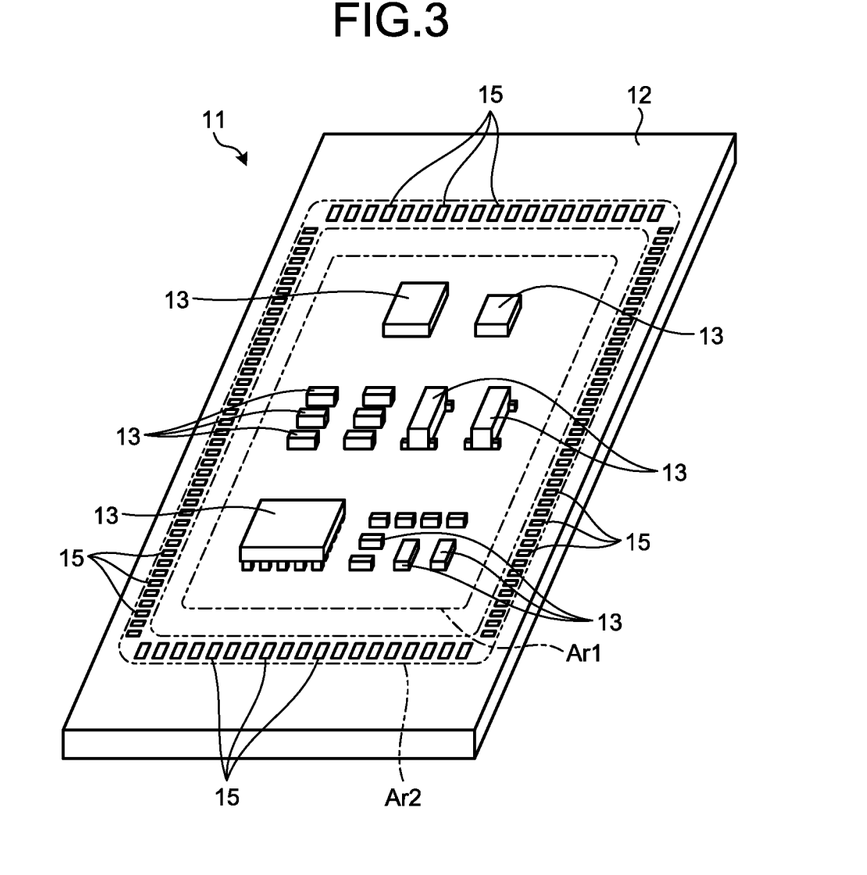
FIG. 3 is a diagram illustrating the medical circuit board.
Figure 4:
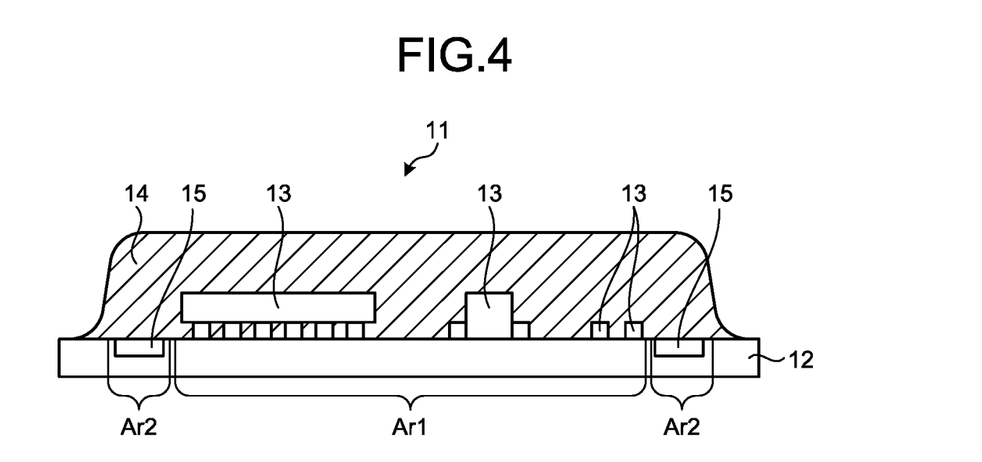
FIG. 4 is a diagram illustrating the medical circuit board.
Figure 5:
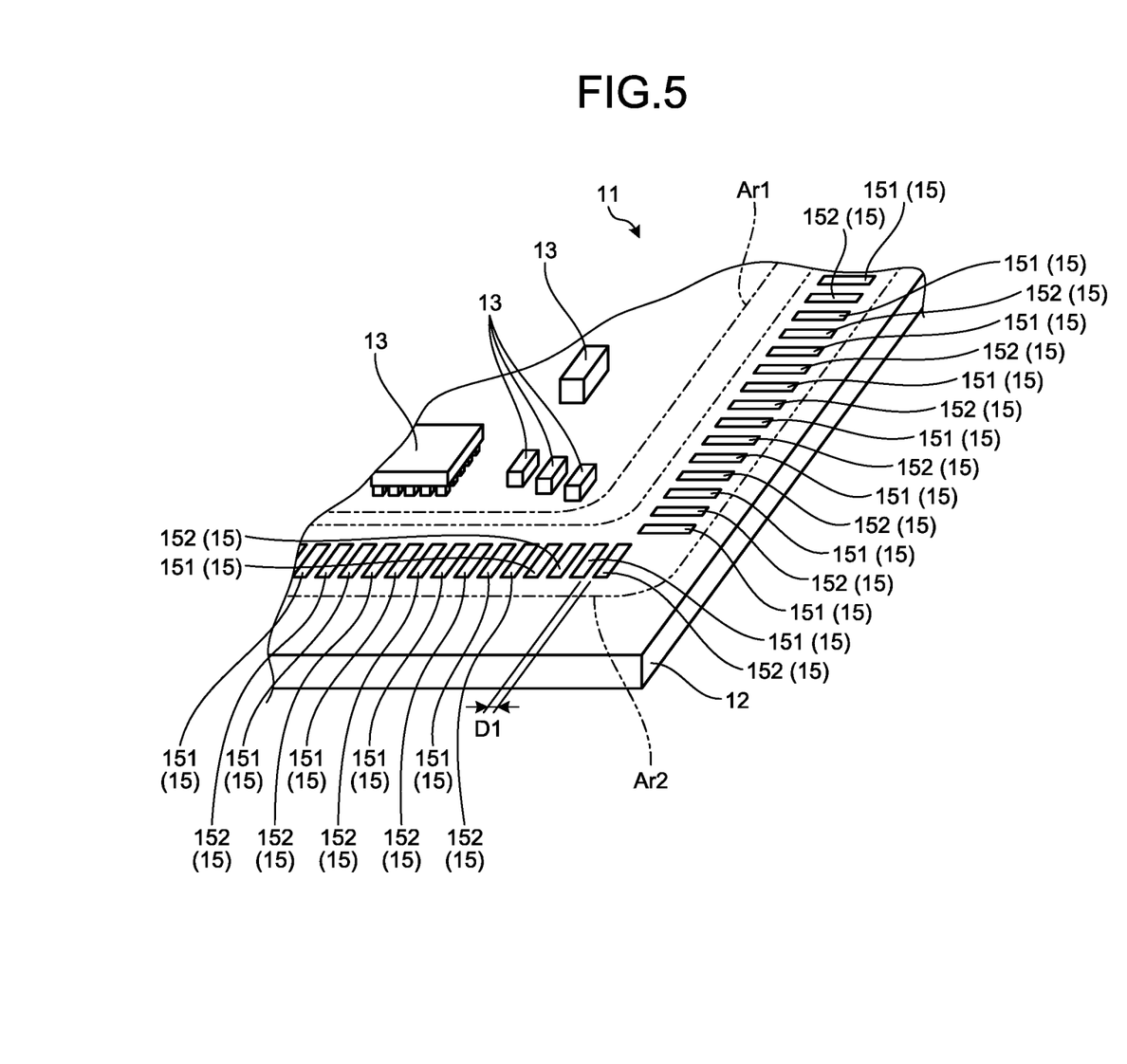
FIG. 5 is a diagram illustrating the medical circuit board.

FIGS. 2 to 5 are diagrams illustrating the medical circuit board 11. Specifically, FIG. 2 is a perspective view of the medical circuit board 11 when viewed from a component surface side. FIG. 3 is a diagram illustrating a state in which a sealing member 14 is removed from the state illustrated in FIG. 2. FIG. 4 is a cross-sectional view of the medical circuit board 11. In FIG. 4, for convenience of explanation, only the sealing member 14 is hatched. FIG. 5 is an enlarged view of a part of FIG. 3.

The medical circuit board 11 includes a substrate 12 (FIGS. 2 to 5), a plurality of electronic components 13 (FIGS. 3 to 5), the sealing member 14 (FIGS. 2 and 4), a detection unit 15 (FIGS. 3 to 5).

The substrate 12 is made of an insulating material such as a glass epoxy resin and is a plate body having a rectangular shape in plan view. A wiring pattern 12*a* (see FIG. 6) composed of a copper foil or the like is formed on the substrate 12. Here, a wiring pattern 12*a* includes tracks (wiring portions), lands, pads, and the like. That is, the substrate 12 is configured as a single layer or multilayered printed circuit board.

The plurality of electronic components 13 are configured to include a driving circuit for driving an image sensor (not illustrated) provided in the camera head 5, a plurality of regulators 131 (see FIG. 7) for generating each power supply voltage necessary for driving other electronic components 13, or the like. The plurality of electronic components 13 are mounted in a mounting area Ar1 (FIGS. 3 to 5) of a substantially central portion of a component surface of the substrate 12, and are electrically connected to wiring patterns 12*a*, respectively. In FIGS. 3 and 5, the mounting area Ar1 is indicated by a one-dot chain line. Further, in FIGS. 3 and 5, in the component surface of the substrate 12, an annular area (hereinafter, described as a detection area Ar2) extending over the whole circumference in a circumferential direction surrounding the mounting area Ar1 to form a rectangle is indicated by a two-dot chain line.

The sealing member 14 is made of a thermosetting type resin or a condensation type resin such as a silicone-based resin or condensation resin, and is provided to be in close contact with the whole of the mounting area Ar1 and the detection area Ar2 on the component surface of the substrate 12 by potting or coating. The sealing member 14 covers the plurality of electronic components 13 mounted in the mounting area Ar1 and the detection unit 15 formed in the detection area Ar2, and the plurality of electronic components 13 and the detection unit 15 are sealed to the substrate 12 with the sealing member 14.

The first transmission cable 6 (including the connectors CN1 and CN2) is a part to be subjected to sterilization treatment by an autoclave and disinfection treatment by a disinfectant solution, prior to observing an inside of a living body. Therefore, the sealing member 14 may be used to protect the plurality of electronic components 13 from steam at the time of the sterilization treatment by the autoclave and liquids such as the disinfectant solution at the time of the disinfection treatment.

The detection unit 15 is the wiring pattern formed on the substrate 12 and detects an infiltration of a liquid into an interface between the substrate 12 and the sealing member 14.

Here, when the sterilization treatment by the autoclave, or the like is performed many times, a gap is likely to be formed at the interface between the substrate 12 and the sealing member 14 at an outer edge portion of the sealing member 14. That is, there is a possibility that a liquid infiltrates into the mounting area Ar1 (the plurality of electronic components 13) via the gap. The detection unit 15 is used to detect a situation in which a liquid is likely to infiltrate into the mounting area Ar1.

A method (hereinafter, described as a liquid infiltration detection method) for detecting the infiltration of the liquid into the interface by the detection unit 15 will be described below.

As illustrated in FIG. 5, the detection unit 15 includes a plurality of first electrode units 151 and a plurality of second electrode units 152.

As illustrated in FIG. 5, in the detection area Ar2, the first and second electrode units 151 and 152 are alternately arranged over the whole circumference in the circumferential direction surrounding the mounting area Ar1.

All separation distance D1 (FIG. 5) between the first and second electrode units 151 and 152 are set to be equal.

Figure 6:
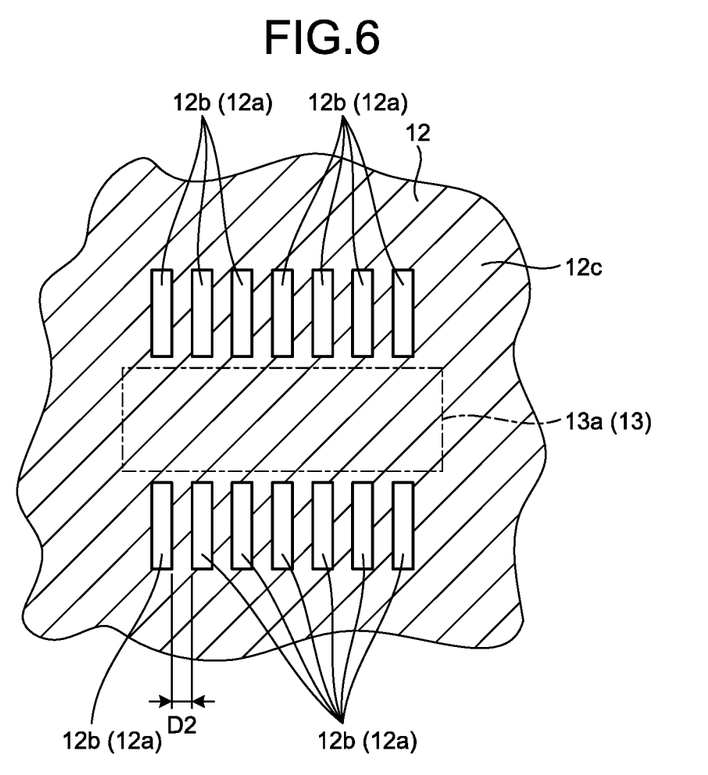
FIG. 6 is a diagram for explaining a separation distance between first and second electrode units.

FIG. 6 is a diagram for explaining the separation distance D1 between the first and second electrode units 151 and 152. Specifically, FIG. 6 is a diagram illustrating the respective lands 12b (wiring patterns 12a) to which each pin of an electronic component 13a having the narrowest pin pitch among the plurality of electronic components 13 is electrically connected in the mounting area Ar1. In FIG. 6, a substrate resist 12c applied on the substrate 12 is indicated by a diagonal line. Here, the substrate resist 12c is a solder resist including a general acrylate resin as a main component. In FIGS. 2 to 5, for convenience of explanation, the substrate resist 12c is not illustrated.

The separation distance D1 (FIG. 5) between the first and second electrode units 151 and 152 is set to be equal to a separation distance D2 (FIG. 6) of the respective lands 12b (wiring patterns 12a) to which each pin of the electronic component 13a having the narrowest pin pitch among the plurality of electronic components 13 is electrically connected. In other words, the separation distance D1 between the first and second electrode units 151 and 152 is set to be a minimum pitch in the wiring pattern 12a. The separation distance D1 is not limited to the same distance as the separation distance D2, but may be set to be smaller than the separation distance D2 (smaller than the minimum pitch in the wiring pattern 12a).

Liquid Infiltration Detection Method

Next, a method of detecting an infiltration of a liquid by a detection unit 15 will be described with reference to FIG. 7.

Figure 7:
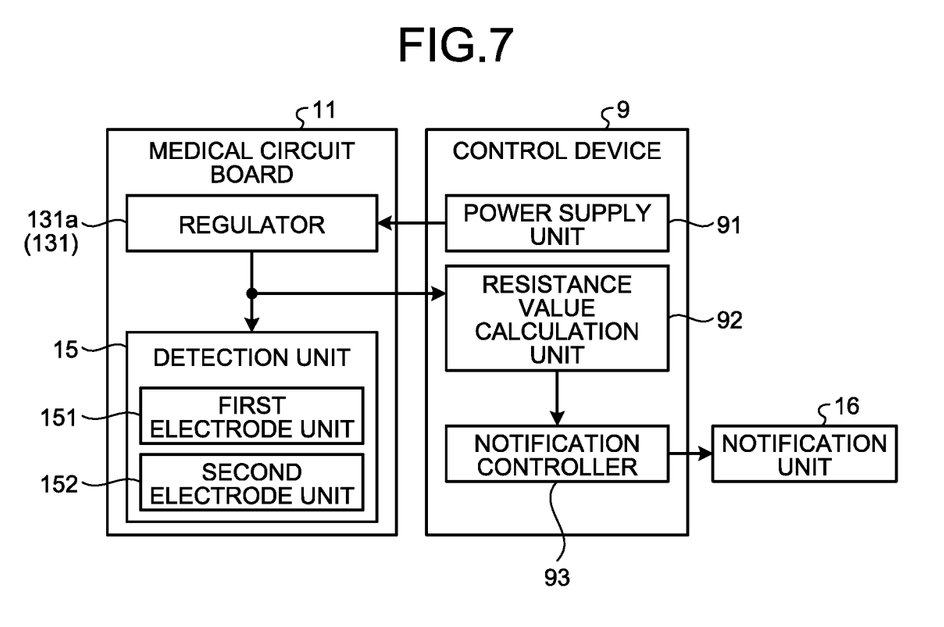
FIG. 7 is a block diagram for explaining a method of detecting an infiltration of a liquid by a detection unit.

FIG. 7 is a block diagram for explaining a method of detecting an infiltration of a liquid by a detection unit. In FIG. 7, only essential parts for explaining the liquid infiltration detection method are illustrated.

A potential difference is present between the first and second electrode units 151 and 152. Specifically, the medical circuit board 11 is electrically connected to the control device 9 by mounting the connector CN1 to the control device 9. A voltage is applied between the first and second electrode units 151 and 152 from a regulator 131a (FIG. 7) of the plurality of regulators 131. Here, the regulator 131a is a regulator (regulator supplying an operating voltage to the electronic component 13 operated by the highest operating voltage among the plurality of electronic components 13) of the plurality of regulators 131 that generates the highest operating voltage based on the driving power supplied from the control device 9 (power supply unit 91 (FIG. 7)). That is, the highest operating voltage among the operating voltages supplied to the plurality of electronic components 13 is applied between the first and second electrode units 151 and 152. It is to be noted that the voltage applied between the first and second electrode units 151 and 152 is not limited to be the same voltage as the highest operating voltage among the operating voltages supplied to the plurality of electronic components 13, but may be set to be larger than the operating voltage.

Meanwhile, when a liquid infiltrates into the interface between the substrate 12 and the sealing member 14, a resistance value between the first and second electrode units 151 and 152 is changed in response to the amount of the liquid. For this reason, when the above-described operating voltage is applied between the first and second electrode units 151 and 152 by the regulator 131a, the control device 9 (resistance value calculation unit 92 (FIG. 7)) calculates the resistance value. The control device 9 (notification controller 93 (FIG. 7)) compares the calculated resistance value with a threshold value, and controls an operation of a notification unit 16 (FIG. 7) when the resistance value becomes equal to or less than the threshold value, and allows the notification unit 16 to notify information on the possibility that the liquid infiltrates from the interface between the substrate 12 and the sealing member 14 into the mounting area Ar1.

The notification unit 16 may be configured as the display device 7, may be configured to notify the above-described information as the display image, may be configured as a light emitting diode (LED) or the like, and may be configured to notify the above-described information by turning on or blinking. In addition, the notification unit 16 may be configured as a speaker, and may be configured to notify the above-described information by voice.

According to the first embodiment described above, the following effects are obtained.

In the medical circuit board 11 according to the first embodiment, the plurality of electronic components 13 mounted in the mounting area Ar1 on the substrate 12 are covered with the resinous sealing member 14, and are sealed with the sealing member 14 to the substrate 12. Therefore, the sealing member 14 may protect the plurality of electronic components 13 from the steam at the time of the sterilization treatment by the autoclave and the liquid such as the disinfectant solution at the time of the disinfection treatment.

In addition, in the medical circuit board 11 according to the first embodiment, the detection unit 15 for detecting the infiltration of the liquid into the interface between the substrate 12 and the sealing member 14 is provided in the detection area Ar2 other than the mounting area Ar1 on the substrate 12. Therefore, even in the situation in which the gap is formed at the interface and the liquid is likely to infiltrate into the mounting area Ar1 via the gap, the detection unit 15 may detect the situation at an early stage.

In particular, the detection unit 15 is sealed with the sealing member 14 together with the plurality of electronic component 13 to the substrate 12. For this reason, for example, in the configuration in which all the detection units 15 are not sealed with the sealing member 14, the liquid is detected even when no gap is formed at the interface between the substrate 12 and the sealing member 14, the detection unit 15 is sealed with the sealing member 14, such that the structure of detecting the above-described situation may be easily realized.

In addition, in the medical circuit board 11 according to the first embodiment, the first and second electrode units 151 and 152 configuring the detection unit 15 are alternately arranged in the circumferential direction over the whole circumference in the circumferential direction surrounding the mounting area Ar1. Therefore, even if the gap occurs at the interface between the substrate 12 and the sealing member 14 at any position on the whole circumference of the outer periphery of the sealing member 14, the detection unit 15 may detect the above-described situation at an early stage.

Among the plurality of electronic components 13, the electronic component 13, which is prone to failure due to a short circuit caused by the infiltration of the liquid is the electronic component 13 to which the highest operating voltage is supplied.

In the medical circuit board 11 according to the first embodiment, the potential difference provided between the first and second electrode units 151 and 152 is set to be the same as the highest operating voltage among the operating voltages supplied to the plurality of electronic components 13. That is, by applying the same operating voltage as the electronic component 13 which is prone to failure between the first and second electrode units 151 and 152, the first and second electrode units 151 and 152 are easily short-circuited from each other, and as a result, it is possible to avoid the failure of the electronic component 13, eventually, the failure of all the electronic components 13 in advance.

Among the plurality of electronic components 13, the electronic component 13 which is prone to failure due to the short circuit caused by the infiltration of the liquid is the electronic component 13a having the narrowest pin pitch.

In the medical circuit board 11 according to the first embodiment, the separation distance D1 between the first and second electrode units 151 and 152 is set to be equal to the separation distance D2 between the respective lands 12b (wiring patterns 12a) to which the respective pins of the electronic component 13a are electrically connected. That is, by setting the separation distance D1 between the first and second electrode units 151, 152 to be equal to the separation distance D2 of the respective lands 12b to which the respective pins of the electronic component 13a, which is prone to failure, are electrically connected, the first and second electrode units 151 and 152 are easily short-circuited from each other, and as a result, it is possible to avoid the failure of the electronic component 13a, eventually, the failure of all the electronic components 13 in advance.

In addition, the medical endoscope apparatus 1 according to the first embodiment includes the notification unit 16 that notifies the detection results by the detection unit 15. As a result, it is possible to notify the user of the above-described situation at an early stage.

Second Embodiment

Next, a second embodiment will be described below.

In the following description, the same reference numerals are given to the same components as those of the first embodiment described above, and a detailed description thereof will be omitted or simplified.

Figure 8:
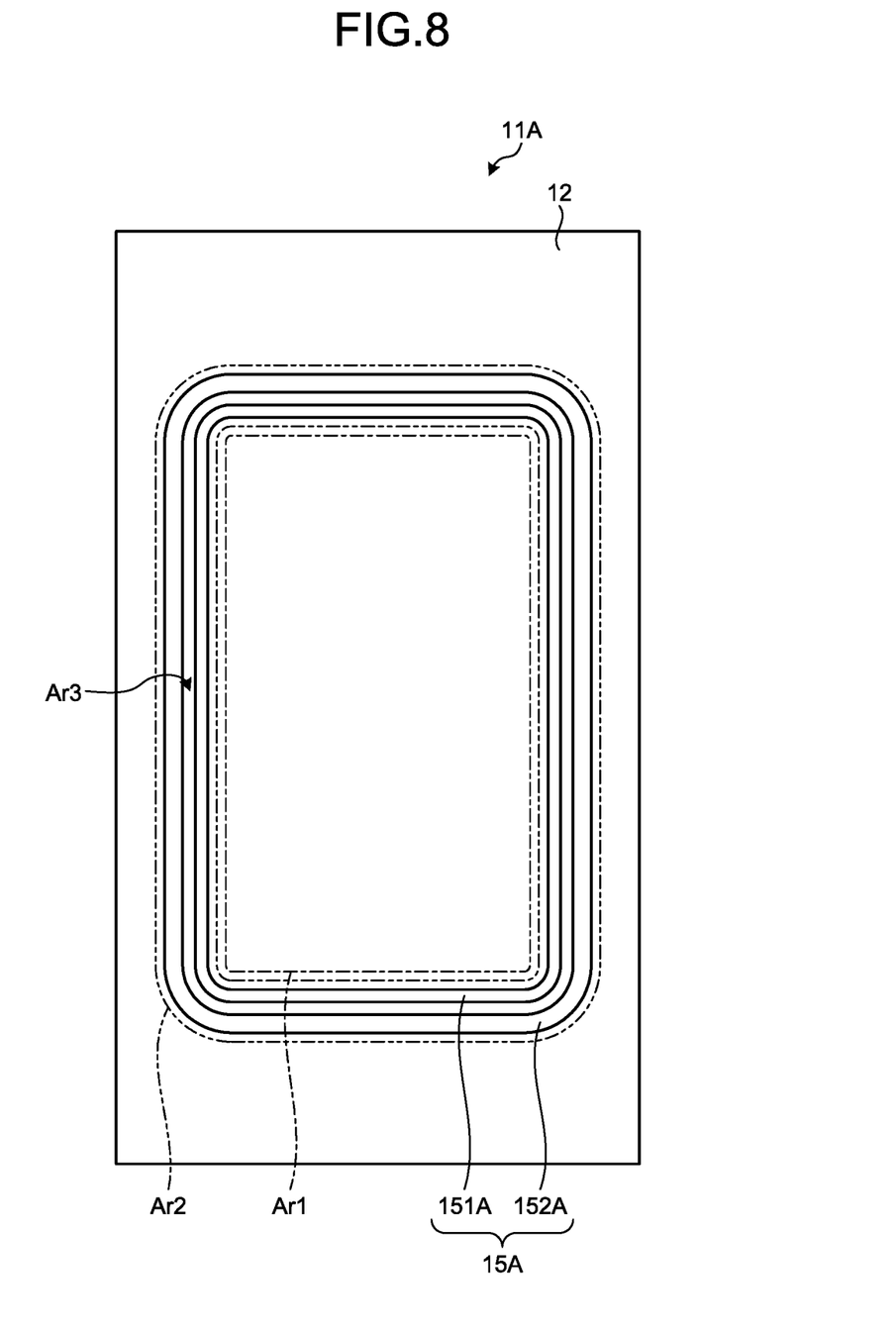
FIG. 8 is a diagram illustrating a medical circuit board according to a second embodiment.
Figure 9:
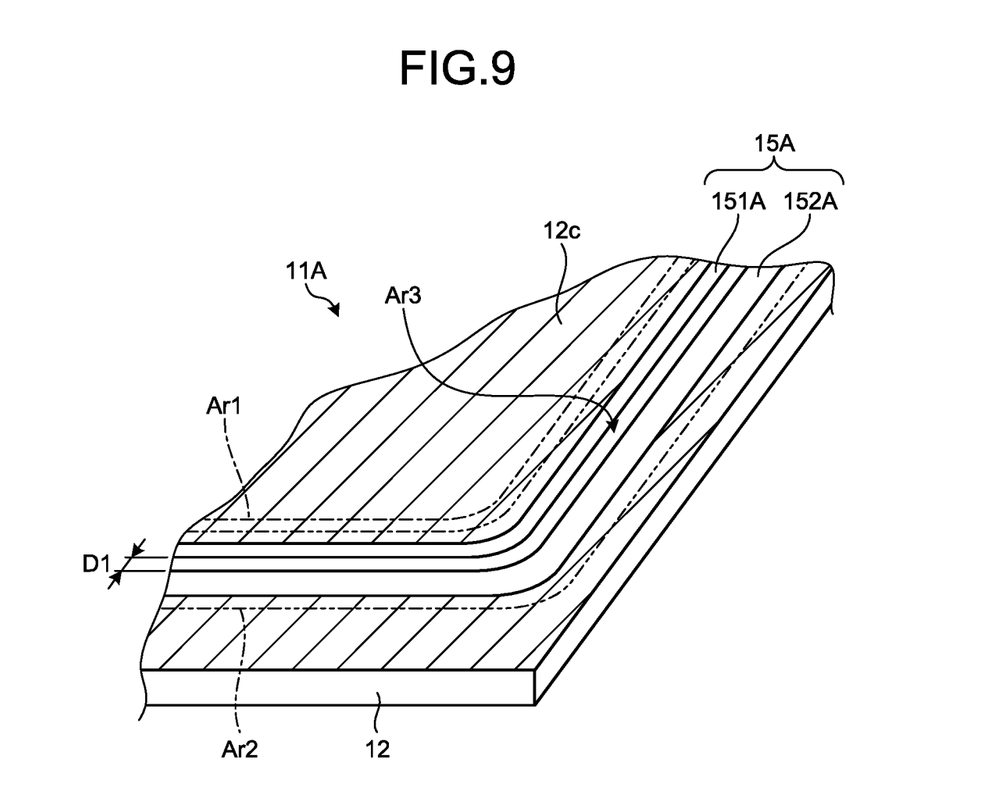
FIG. 9 is a diagram illustrating the medical circuit board according to the second embodiment.

FIGS. 8 and 9 are diagrams illustrating a medical circuit board 11A according to the second embodiment. Specifically, FIG. 8 is a diagram of the medical circuit board 11 when viewed from a component surface side. In FIG. 8, for convenience of explanation, a plurality of electronic components 13, a sealing member 14, and a substrate resist 12c are omitted. FIG. 9 is an enlarged view of a part of FIG. 8. In FIG. 9, a substrate resist 12c applied on the substrate 12 is indicated by a diagonal line.

As illustrated in FIG. 8 or 9, in the medical circuit board 11A according to the second embodiment, a detection unit 15A different from the detection unit 15 is adopted for the medical circuit board 11 (FIGS. 2 to 5) described in the first embodiment described above.

Like the detection unit 15 described in the first embodiment described above, the detection unit 15A is a wiring pattern formed on the substrate 12, and detects an infiltration of a liquid into an interface between the substrate 12 and the sealing member 14. As illustrated in FIG. 8 or 9, the detection unit 15A includes a first electrode unit 151A and a second electrode unit 152A.

The first electrode unit 151A has an annular shape extending along a circumferential direction surrounding a mounting area Ar1 to form a rectangle in a detection area Ar2.

The second electrode unit 152A has an annular shape extending along the circumferential direction surrounding the first electrode unit 151A to form the rectangle in the detection area Ar2.

A separation distance D1 (FIG. 9) between the first and second electrode units 151A and 152A is set to be the same distance as that in the first embodiment described above.

Here, as illustrated in FIG. 9, an area between the first and second electrode units 151A and 152A is an uncoated area Ar3 to which the substrate resist 12c is not applied. That is, the uncoated area Ar3 has an annular shape extending in the circumferential direction surrounding the mounting area Ar1. Like the first embodiment described above, the sealing member 14 according to the second embodiment is provided in the whole of the mounting area Ar1 and the detection area Ar2 (including the uncoated area Ar3). That is, the sealing member 14 covers the plurality of electronic components 13 mounted in the mounting area Ar1 and the detection unit 15A formed in the detection area Ar2, and the plurality of electronic components 13 and the detection unit 15A are sealed with the sealing member 14 to the substrate 12.

Since a method of detecting an infiltration of a liquid by the detection unit 15A is the same as that in the first embodiment, a detailed explanation of the method will be omitted, but the method is a method for providing a potential difference between first and second electrode units 151A and 152A to detect a change in a resistance value between the first and second electrode units 151A and 152A.

According to the second embodiment described above, in addition to the same effects as those of the first embodiment described above, the following effects are obtained.

In the medical circuit board 11A according to the second embodiment, the first electrode unit 151A has an annular shape extending in the circumferential direction surrounding the mounting area Ar1. In addition, the second electrode unit 152A has an annular shape extending in the circumferential direction surrounding the first electrode unit 151A. Therefore, as compared with the detection unit 15 described in the first embodiment described above, the configuration of the detection unit 15A may be simplified and the area of the substrate 12 may also be reduced.

Meanwhile, an adhesion between the substrate 12 made of a glass epoxy resin and the sealing member 14 made of a silicone-based resin is generally greater than that between the sealing member 14 and the substrate resist 12c which is a solder resist made of an acrylate resin as a main component.

In the medical circuit board 11A according to the second embodiment, an uncoated area Ar3 to which the substrate resist 12c is not applied is provided between the first and second electrode units 151A and 152A. That is, the sealing member 14 is in close contact with the substrate 12 in the annular uncoated area Ar3 extending in the circumferential direction surrounding the mounting area Ar1. As a result, it is possible to improve the adhesion between the substrate 12 and the sealing member 14 in the uncoated area Ar3, and suppress the infiltration of the liquid into the mounting area Ar1.

Third Embodiment

Next, a third embodiment will be described below.

In the following description, the same reference numerals are given to the same components as those of the second embodiment described above, and a detailed description thereof will be omitted or simplified.

Figure 10:
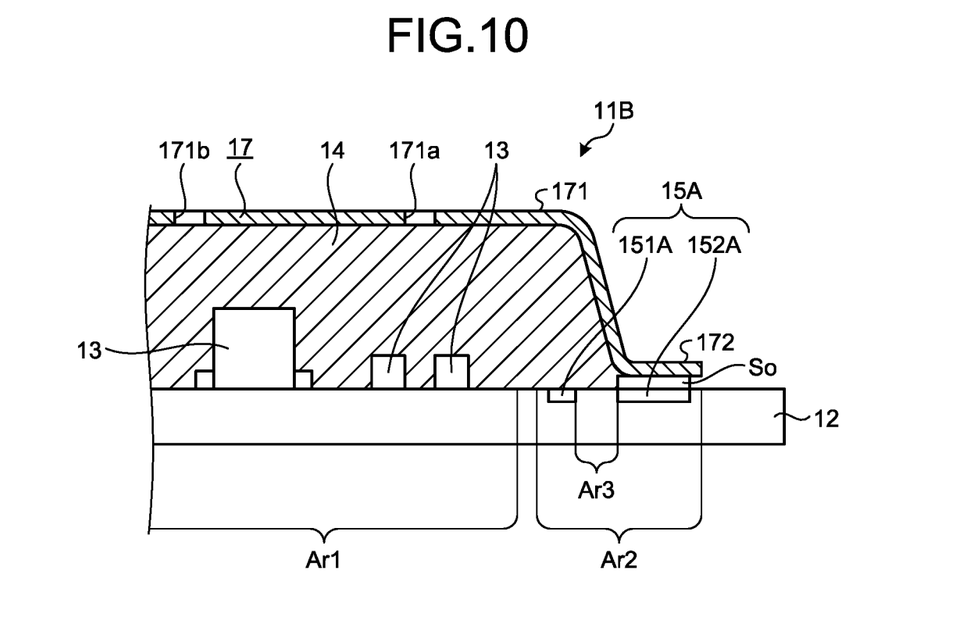
FIG. 10 is a diagram illustrating a medical circuit board according to a third embodiment.

FIG. 10 is a diagram illustrating a medical circuit board 11B according to a third embodiment; specifically, FIG. 10 is a cross-sectional view of the medical circuit board 11B. In FIG. 10, for convenience of explanation, only a sealing member 14 and a cover member 17 are hatched.

As illustrated in FIG. 10, in the medical circuit board 11B according to the third embodiment, a cover member 17 is added to the medical circuit board 11A (FIGS. 8 and 9) described in the second embodiment described above.

The cover member 17 is made of a metal material and serves as a shield member for shielding electromagnetic noise. As illustrated in FIG. 10, the cover member 17 includes a cover main body 171 and a fixed portion 172.

The cover main body 171 has substantially a rectangular parallelepiped container shape. A container-shaped bottom portion of the cover main body 171 has a planar size which is larger than the first electrode unit 151A and slightly smaller than the second electrode unit 152A in plan view (viewed from the component surface side of the medical circuit board 11B). In addition, as illustrated in FIG. 10, the bottom portion is provided with a filling hole 171a for filling the cover main body 171 with an uncured thermosetting resin (sealing member 14) and an air vent hole 171b for removing air in the cover main body 171 at the time of the filling.

The fixed portion 172 is a portion that protrudes outward from edges of four sides of an opening portion of the cover main body 171, and has a rectangular frame shape. The fixed portion 172 has substantially the same planar size as the second electrode unit 152A in plan view.

The cover member 17 is attached to the substrate 12 by fixing the fixed portion 172 to the second electrode unit 152A by solder So (FIG. 10). In this state, the cover member 17 covers the plurality of electronic components 13, and shields electromagnetic noise affecting the plurality of electronic components 13 from the outside or electromagnetic noise affecting the outside from the plurality of electronic components 13 It is to be noted that the solder So is provided over the whole surface of the second electrode unit 152A (the whole surface of the fixed portion 172).

The sealing member 14 according to the third embodiment is provided as described below after the cover member 17 is attached to the substrate 12 as described above.

That is, an operator inserts an injection needle of a syringe into the filling hole 171a using the syringe (not illustrated) that is filled with the uncured thermosetting resin (sealing member 14) in advance, and fills the cover main body 171 with the thermosetting resin. At the time of the filling, the air in the cover main body 171 is discharged from the air vent hole 171b. The operator fills the thermosetting resin and then heats the thermosetting resin so that the thermosetting resin cures.

That is, the sealing member 14 according to the third embodiment is provided in the whole of the mounting area Ar1 and a partial area of the detection area Ar2. That is, the sealing member 14 covers the plurality of electronic components 13 mounted in the mounting area Ar1 and a part (first electrode unit 151A) of the detection unit 15A formed in the detection area Ar2, and the plurality of electronic components 13 and the first electrode unit 151A are sealed with the sealing member 14 to the substrate 12.

According to the third embodiment described above, in addition to the same effects as those of the second embodiment described above, the following effects are obtained.

In the medical circuit board 11B according to the third embodiment, the cover member 17 is added. Therefore, both of the sealing member 14 and the cover member 17 may protect the plurality of electronic components 13 from the liquid, and as a result the lifespan of the plurality of electronic components 13 may be prolonged.

Fourth Embodiment

Next, a fourth embodiment will be described below.

In the following description, the same reference numerals are given to the same components as those of the above-described first embodiment, and a detailed description thereof will be omitted or simplified.

Figure 11:
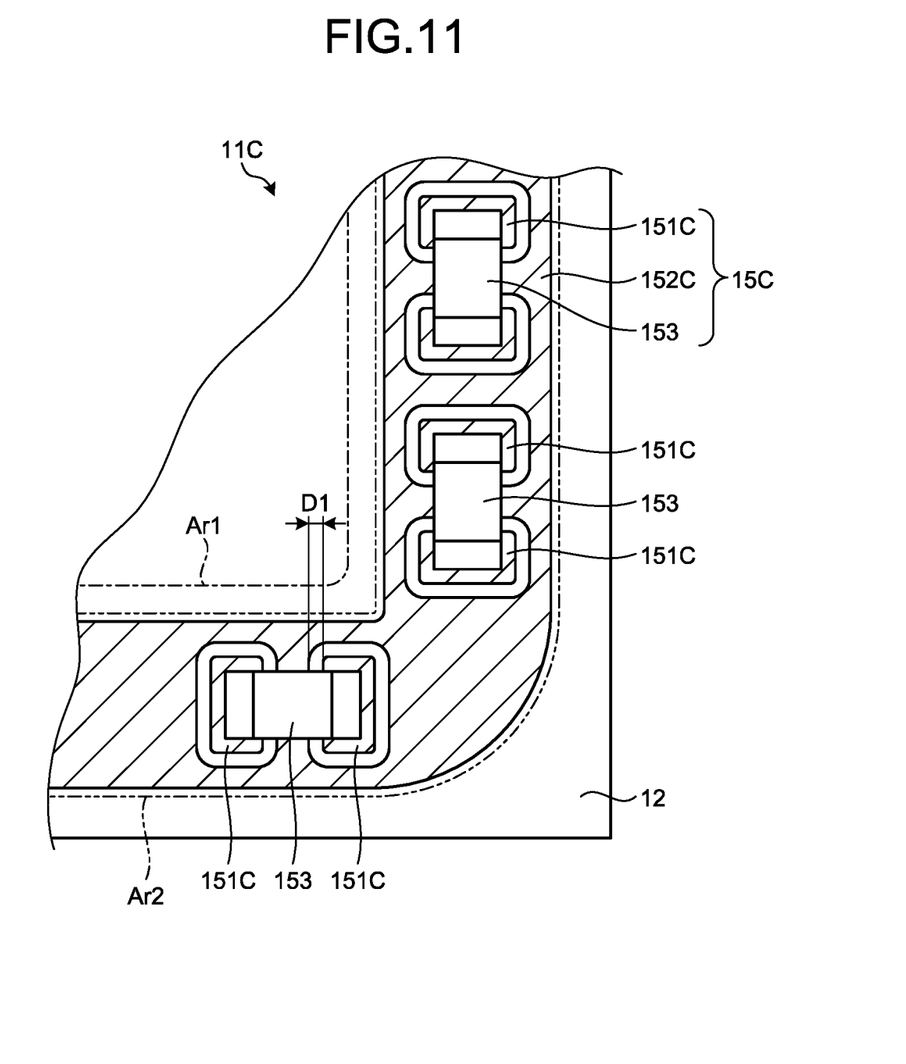
FIG. 11 is a diagram illustrating a medical circuit board according to a fourth embodiment.

FIG. 11 is a diagram illustrating a medical circuit board 11C according to a fourth embodiment. Specifically, FIG. 11 is a diagram illustrating a main part of the medical circuit board 11C. In FIG. 11, for convenience of explanation, a plurality of electronic components 13, a sealing member 14, and a substrate resist 12c are omitted. In FIG. 11, for convenience of explanation, first and second electrode units 151C and 152C are indicated by a diagonal line.

As illustrated in FIG. 11, in the medical circuit board 11C according to the fourth embodiment, a detection unit 15C different from the detection unit 15 for the medical circuit board 11 (FIGS. 2 to 5) described in the first embodiment described above is adopted.

Like the detection unit 15 described in the first embodiment described above, the detection unit 15C detects an infiltration of a liquid into an interface between a substrate 12 and a sealing member 14. As illustrated in FIG. 11, the detection unit 15C includes a plurality of first electrode units 151C, a second electrode unit 152C, and a plurality of zero Ω resistors 153.

Like the detection unit 15 described in the first embodiment described above, the first electrode unit 151C and the second electrode unit 152C are wiring patterns formed on the substrate 12.

The first electrode unit 151C is arranged along a circumferential direction surrounding a mounting area Ar1 in a detection area Ar2.

The second electrode unit 152C is formed as a solid pattern in substantially the whole area except for the plurality of first electrode units 151C in the detection area Ar2.

A separation distance D1 (FIG. 11) between the first and second electrode units 151C and 152C is set to be the same distance as that in the first embodiment described above.

The plurality of zero Ω resistors 153 are an electronic component mounted on the substrate 12, and are each connected by solder so as to extend over the adjacent first electrode unit 151C.

Like the first embodiment described above, the sealing member 14 according to the second embodiment is provided in the whole of the mounting area Ar1 and the detection area Ar2. That is, the sealing member 14 covers the plurality of electronic components 13 mounted in the mounting area Ar1 and the detection unit 15C formed in the detection area Ar2, and the plurality of electronic components 13 and the detection unit 15C (including the plurality of zero Ω resistors 153) are sealed with the sealing member 14 to the substrate 12.

Since a method of detecting an infiltration of a liquid by the detection unit 15C is the same as that in the first embodiment, a detailed explanation of the method will be omitted, but the method is a method for providing a potential difference between first and second electrode units 151C and 152C to detect a change in a resistance value between the first and second electrode units 151C and 152C.

According to the fourth embodiment described above, in addition to the same effects as those of the first embodiment described above, the following effects are obtained.

In the medical circuit board 11C according to the fourth embodiment, the detection unit 15C includes the plurality of zero Ω resistors 153 each connected by the solder so as to extend over the adjacent first electrode unit 151C. That is, since the plurality of zero Ω resistors 153 are interposed in the sealing member 14, the plurality of zero Ω resistors 153 may improve an adhesion between the substrate 12 and the sealing member 14. In addition, it is also possible to improve the detection capability against the elution of the solder (the solder between the first electrode unit 151C and the zero Ω resistor 153) to the infiltrated liquid.

Fifth Embodiment

Next, a fifth embodiment will be described below.

In the following description, the same reference numerals are given to the same components as those of the above-described first embodiment, and a detailed description thereof will be omitted or simplified.

Figure 12:
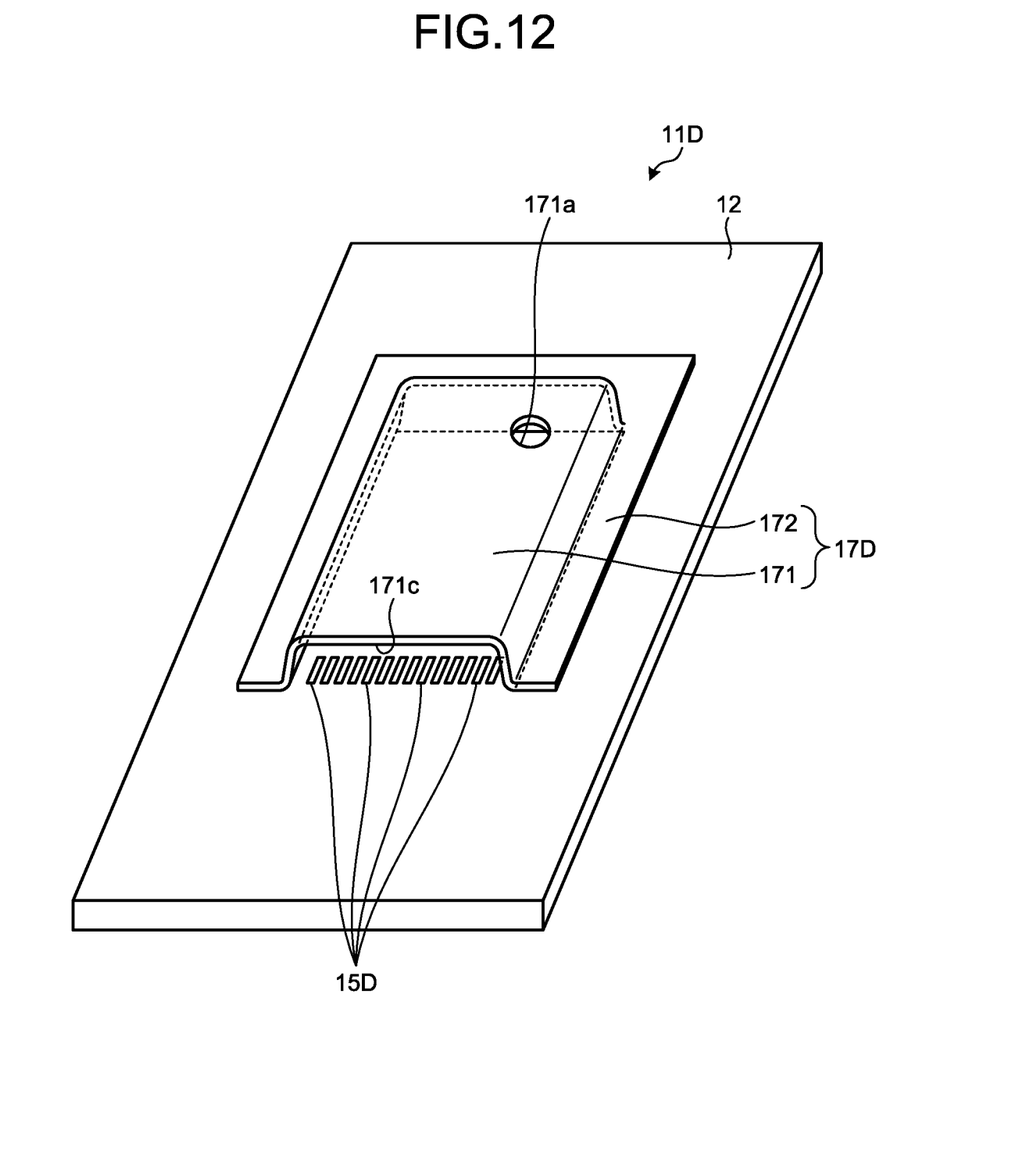
FIG. 12 is a diagram illustrating a medical circuit board according to a fifth embodiment.
Figure 13:
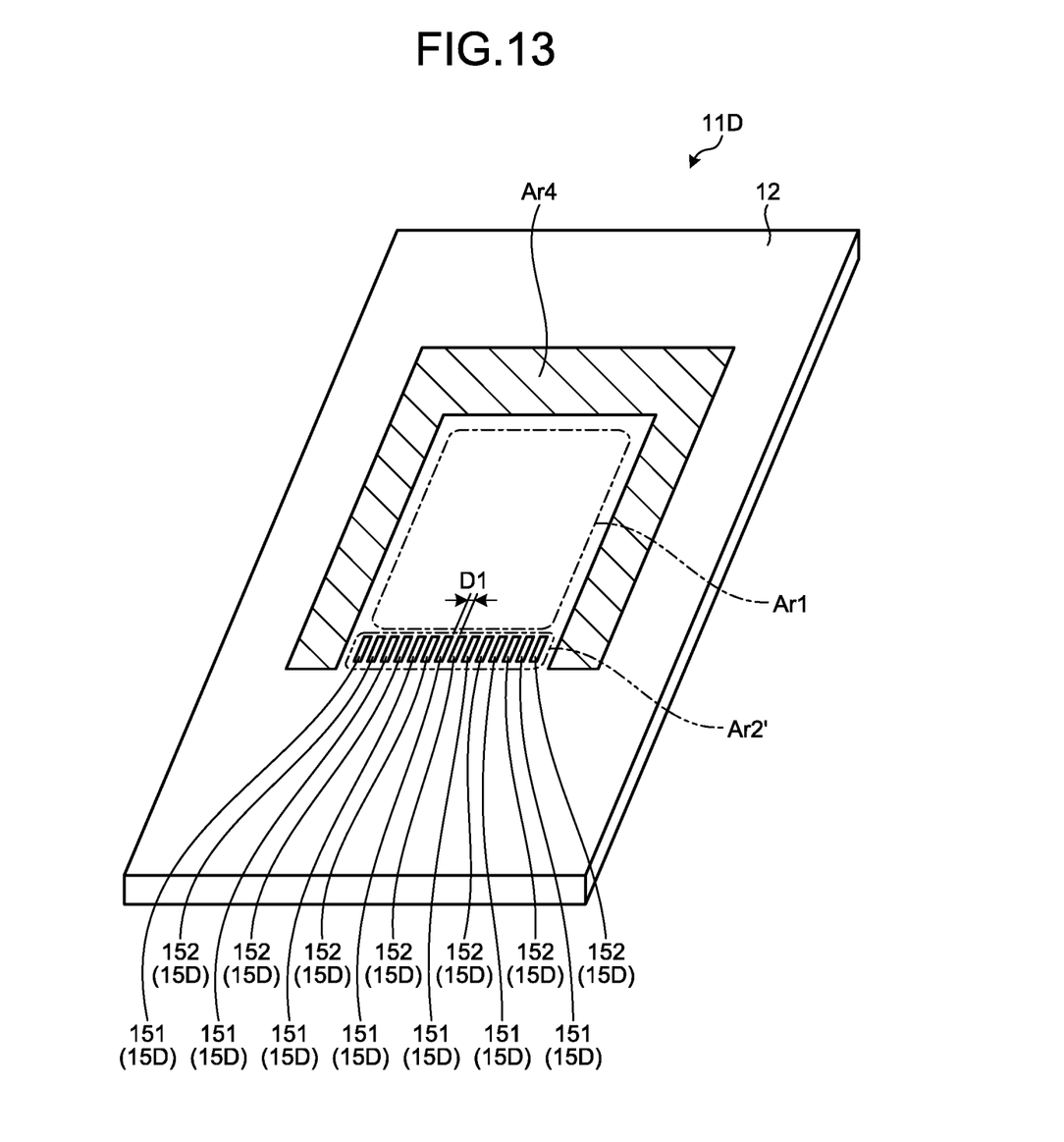
FIG. 13 is a diagram illustrating the medical circuit board according to the fifth embodiment.

FIGS. 12 and 13 are diagrams illustrating a medical circuit board 11D according to a fifth embodiment. Specifically, FIG. 12 is a perspective view of the medical circuit board 11D when viewed from a component surface side. In FIG. 12, for convenience of explanation, a plurality of electronic components 13, a sealing member 14, and a substrate resist 12c are omitted. FIG. 13 is a diagram illustrating a state in which a cover member 17D is removed from the state illustrated in FIG. 12. In FIG. 13, for convenience of explanation, an area Ar4 to which the cover member 17D is attached is hatched.

As illustrated in FIG. 12 or 13, in a medical circuit board 11D according to the fifth embodiment, a detection unit 15D different from the detection unit 15 for the medical circuit board 11 (FIGS. 2 to 5) described in the first embodiment is adopted and a cover member 17D is added.

Like the detection unit 15 described in the first embodiment described above, the detection unit 15D is a wiring pattern formed on the substrate 12, and detects an infiltration of a liquid into an interface between the substrate 12 and the sealing member 14. As illustrated in FIG. 12 or 13, similar to the detection unit 15 described in the first embodiment, the detection unit 15A includes a plurality of first electrode units 151 and a plurality of second electrode units 152.

Here, as illustrated in FIG. 13, the detection area Ar2' according to the fifth embodiment is an area linearly extending along one side of the mounting area Ar1 around the rectangular mounting area Ar1.

The first and second electrode units 151 and 152 according to the fifth embodiment are alternately arranged along the detection area Ar2' in the detection area Ar2'.

A separation distance D1 (FIG. 13) between the first and second electrode units 151 and 152 is set to be the same distance as that in the first embodiment described above. In addition, since a method of detecting an infiltration of a liquid by the detection unit 15D is the same as that in the first embodiment, a detailed explanation of the method will be omitted, but the method is a method for providing a potential difference between first and second electrode units 151 and 152 to detect a change in a resistance value between the first and second electrode units 151 and 152.

A cover member 17D has a configuration in which a part of the cover member 17 (the cover main body 171 and the fixed portion 172) is omitted from the cover member 17 described in the second embodiment described above. More specifically, the cover main body 171 of the cover member 17D has a configuration in which one side surface of the container-like cover main body 171 described in the above-described first embodiment is omitted. In addition, the fixed portion 172 of the cover member 17D has a U-letter shape in plan view (as viewed from the component surface side of the medical circuit board 11D). In the cover member 17D, an air vent hole 171b is also omitted.

The cover member 17D is in a posture in which an opening portion having a U-letter shape in plan view in the fixed portion 172 faces the detection unit 15D side, and the fixed portion 172 adheres to an area Ar4 by a double-sided tape (not illustrated) having heat resistance and insulation to be attached to the substrate 12. In this state, the cover member 17D covers the mounting area Ar1 and the detection area Ar2' in plan view. Like the cover member 17 described in the third embodiment described above, the cover member 17D covers the plurality of electronic components 13, and shields electromagnetic noise affecting the plurality of electronic components 13 from the outside or electromagnetic noise affecting the outside from the plurality of electronic components 13. It is to be noted that the above-described double-sided tape is provided over the whole surface (the whole surface of the fixed portion 172) of the area Ar4.

The sealing member 14 according to the fifth embodiment is provided as described below after the cover member 17D is attached to the substrate 12 as described above.

That is, an operator inserts an injection needle of a syringe into the filling hole 171a using the syringe (not illustrated) that is filled with the uncured thermosetting resin (sealing member 14) in advance, and fills the cover main body 171 with the thermosetting resin. At the time of the filling, the air in the cover main body 171 is discharged through an opening portion 171c (FIG. 12) surrounded by the cover main body 171 and the substrate 12. The operator fills the thermosetting resin and then heats the thermosetting resin so that the thermosetting resin cures.

That is, the sealing member 14 according to the fifth embodiment is provided in the whole of the mounting area Ar1 and a partial area of the detection area Ar2'. The sealing member 14 covers the plurality of electronic components 13 mounted in the mounting area Ar1 and the detection unit 15D formed in the detection area Ar2', and the plurality of electronic components 13 and the detection unit 15D are sealed with the sealing member 14 to the substrate 12.

Even when the medical circuit board 11D according to the fifth embodiment described above is adopted, the same effects as those of the first and third embodiments described above are obtained.

Other Embodiments

Although the embodiments for carrying out the present disclosure have been described so far, the present disclosure should not be limited only by the first to fifth embodiments described above.

In the first to fifth embodiments described above, the medical circuit board according to the present disclosure is used for the medical endoscope apparatus 1 using the rigid endoscope, but is not limited to thereto.

For example, the medical circuit board according to the present disclosure may be used for a medical endoscope apparatus using a flexible endoscope. In addition, the medical circuit board according to the present disclosure may also be adopted for a medical observation device (for example, refer to Japanese Patent Application Laid-Open No. 2016-42981) for enlarging and capturing a predetermined range of vision of an inside of a subject (an inside of a living body) or a surface of a subject (a surface of a living body).

In addition, the shape of the medical circuit board according to the present disclosure is not limited to the rectangular shape in plan view, and may be a circle or other irregular shapes, or may be a curved surface shape instead of a flat surface. In addition, even the mounting area Ar1 is not limited to the rectangular shape and may be an irregular shape. Furthermore, the mounting area Ar1 surrounded by the detection area Ar2 and sealed with the sealing member 14 may be one or plural. Furthermore, the sealing member 14 may seal a plurality of detection area s Ar2 surrounding the mounting area Ar1.

In the first to fifth embodiments described above, if it is determined that there is a possibility that a liquid may infiltrate into the mounting area Ar1 from the interface between the substrate 12 and the sealing member 14, the notification controller 93 allows the notification unit 16 to notify the information to that effect, but the embodiments are not limited thereto. For example, the notification unit 16 may notify information indicating that the liquid does not infiltrate from the interface between the substrate 12 and the sealing member 14 into the mounting area Ar1 or the notification unit 16 may notify information indicating the infiltration levels of the liquid according to the resistance value calculated by the resistance value calculation unit 92.

In the first to fifth embodiments described above, the resistance value calculation unit 92 and the notification controller 93 are provided in the control device 9, but the present embodiments are not limited thereto, and the resistance value calculation unit 92 and the notification controller 93 may be provided outside the control device 9 (for example, the camera head 5 and the connectors CN1 and CN2, and the like).

The uncoated area Ar3 described in the second and third embodiments is not necessarily provided only in the medical circuit boards 11A and 11B described in the second and third embodiments described above, but may be provided in the medical circuit boards 11, 11C, and 11D described in the first, fourth, and fifth embodiments described above.

In the third embodiment described above, the cover member 17 is fixed to the second electrode unit 152A by the solder So, but is not limited thereto, and like the fifth embodiment described above, the cover member 17 may be fixed by the double-sided tape. Similarly, in the fifth embodiment described above, the cover member 17D is attached to the substrate 12 by the double-sided tape, but is not limited thereto, and like the third embodiment described above, the structure of the cover member 17D fixed by the solder So may be adopted.

In the medical circuit board according to the present disclosure, the plurality of electronic components mounted in the mounting area on a substrate are covered with the resinous sealing member and thus are sealed between the electronic components and the substrate by the sealing member. Therefore, the sealing member may protect the plurality of electronic components from the steam at the time of the sterilization treatment by the autoclave and liquids such as the disinfectant solution at the time of the disinfection treatment.

Here, when the sterilization treatment by the autoclave or the disinfection treatment by the disinfectant solution is performed many times, the gap is likely to be formed at the interface between the substrate and the sealing member at the outer edge portion of the sealing member. That is, there is a possibility that the liquid infiltrates into the mounting area (the plurality of electronic components) via the gap.

Here, in the medical circuit board according to the present disclosure, the detection unit for detecting the infiltration of the liquid into the interface between the substrate and the sealing member is provided in the area other than the mounting area on the substrate. Therefore, even in the situation in which the gap is formed at the interface and the liquid is likely to infiltrate into the mounting area via the gap, the detection unit may detect the situation at an early stage.

In particular, at least a part of the detection unit is sealed together with the plurality of electronic components between the detection unit and the substrate by the sealing member. For this reason, for example, in the configuration in which all the detection units are not sealed with the sealing member, the liquid is detected even when no gap is formed at the interface between the substrate and the sealing member, at least one of the detection units is sealed with the sealing member, such that the structure of detecting the above-described situation may be realized.

In addition, since the medical device according to the present disclosure includes the above-described medical circuit board, the medical device exhibits the same action and effect as the above-described medical circuit board. In addition, the medical device includes the notification unit that notifies the detection result of the detection unit. As a result, it is possible to notify the user of the above-described situation at an early stage.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical circuit board, comprising:
   a substrate on which a wiring pattern is formed;
   a plurality of electronic components mounted in a mounting area on the substrate;
   a resinous seal covering the plurality of electronic components, with which the plurality of electronic components are sealed to the substrate; and
   a detector provided in an area other than the mounting area on the substrate and detecting an infiltration of a liquid into an interface between the substrate and the resinous seal, the detector including a first electrode on the substrate and a second electrode on the substrate providing a potential difference between the first electrode and the second electrode, wherein
   the resinous seal covers at least a part of the detector,
   the first electrode has an annular shape extending in a circumferential direction surrounding the mounting area, and
   the second electrode has an annular shape extending in a circumferential direction surrounding the first electrode.

2. The medical circuit board according to claim 1, wherein the potential difference is set to be equal to or higher than a highest operating voltage among operating voltages supplied to the plurality of electronic components.

3. The medical circuit board according to claim 1, wherein a separation distance between and the second electrode is set to be equal to or less than a minimum pitch of the wiring pattern.

4. The medical circuit board according to claim 1, wherein
a part of an area on the substrate is applied with a substrate resist,
an adhesion between the substrate and the resinous seal is higher than that between the resinous seal and the substrate resist,
the substrate includes an uncoated area having an annular shape extending in a circumferential direction surrounding the mounting area that does not include the substrate resist, and
the resinous seal covers the uncoated area.

5. A medical device, comprising:
the medical circuit board according to claim 1; and
an alarm that alerts when the potential difference falls below a threshold value.

6. A medical circuit board, comprising:
a substrate including a wiring pattern;
a plurality of electronic components in a mounting area on the substrate;
a seal that covers the plurality of electronic components to seal the plurality of electronic components to the substrate; and
a detector that detects an infiltration of a liquid into an interface between the substrate and the seal, the detector being in an area other than the mounting area, the detector including a first electrode on the substrate and a second electrode on the substrate providing a potential difference between the first electrode and the second electrode, wherein
the seal covers at least a part of the detector,
the first electrode has an annular shape extending in a circumferential direction surrounding the mounting area, and
the second electrode has an annular shape extending in a circumferential direction surrounding the first electrode.

7. The medical circuit board according to claim 6, wherein the potential difference is set to be equal to or higher than a highest operating voltage among operating voltages supplied to the plurality of electronic components.

8. The medical circuit board according to claim 6, wherein a separation distance between the first electrode and the second electrode is set to be equal to or less than a minimum pitch of the wiring pattern.

9. The medical circuit board according to claim 6, wherein
a substrate resist on part of an area on the substrate,
adhesion between the substrate and the seal is higher than that between the seal and the substrate resist,
the substrate has an uncoated area having an annular shape extending in a circumferential direction surrounding the mounting area and that does not include the substrate resist, and
the seal covers the uncoated area.

10. The medical circuit board according to claim 6, further comprising a cover that serves an electromagnetic shield and covers the seal.

11. The medical circuit board according to claim 10, wherein the cover covers an upper surface and at least one sidewall of the seal.

12. The medical circuit board according to claim 11, wherein the cover covers all sidewalls of the seal.

13. A medical device, comprising:
the medical circuit board according to claim 6; and
an alarm that alerts when the potential difference falls below a threshold value.

* * * * *